(12) United States Patent
Wu et al.

(10) Patent No.: US 11,151,720 B2
(45) Date of Patent: Oct. 19, 2021

(54) PHYSIOLOGICAL INFORMATION DETECTION DEVICE AND PHYSIOLOGICAL INFORMATION DETECTION METHOD

(71) Applicant: NATIONAL CHIAO TUNG UNIVERSITY, Hsinchu (TW)

(72) Inventors: Bing-Fei Wu, Hsinchu (TW); Yun-Wei Chu, Taichung (TW); Po-Wei Huang, Douliu (TW); Meng-Liang Chung, Changhua (TW); Yin-Cheng Tsai, Taoyuan (TW)

(73) Assignee: NATIONAL CHIAO TUNG UNIVERSITY, Hsinchu (TW)

( * ) Notice: Subject to any disclaimer, the term of this patent is extended or adjusted under 35 U.S.C. 154(b) by 132 days.

(21) Appl. No.: 16/732,985

(22) Filed: Jan. 2, 2020

(65) Prior Publication Data

US 2021/0019881 A1    Jan. 21, 2021

(30) Foreign Application Priority Data

Jul. 16, 2019 (TW) .................................. 108125128

(51) Int. Cl.
*G06T 7/00* (2017.01)
*A61B 5/024* (2006.01)

(52) U.S. Cl.
CPC ........ *G06T 7/0012* (2013.01); *A61B 5/02416* (2013.01); *G06T 2207/20048* (2013.01); *G06T 2207/30201* (2013.01)

(58) Field of Classification Search
CPC ......... G06T 7/0012; G06T 2207/30201; G06T 2207/20048; G06T 2207/20021;
(Continued)

(56) References Cited

U.S. PATENT DOCUMENTS

2005/0272984 A1* 12/2005 Huiku .................. A61B 5/4824
600/301
2017/0360377 A1* 12/2017 Rossi ..................... A61B 5/364
(Continued)

FOREIGN PATENT DOCUMENTS

TW        M492140 U      12/2014
TW        I478690 B       4/2015
(Continued)

OTHER PUBLICATIONS

Cheng et al., "Illumination Variation-Resistant Video-Based Heart Rate Measurement Using Joint Blind Source Separation and Ensemble Empirical Mode Decomposition," IIEEE Journal of Biomedical and Health Informatics, 2016, pp. 1-12.
(Continued)

*Primary Examiner* — Siamak Harandi
(74) *Attorney, Agent, or Firm* — Birch, Stewart, Kolasch & Birch, LLP

(57) ABSTRACT

The present invention provides a physiological information detection method for calculating a physiological value by using changes of a dynamic image. The detection method includes: acquiring detection data from a gray-scale value of the dynamic image, and transforming the detection data into frequency data. The detection method further includes: determining whether the frequency data meet a preset condition, and using a transformation model of a corresponding transformation combination accordingly to transform the frequency data into a physiological value. The present invention further provides a physiological information detection device applying the detection method.

28 Claims, 5 Drawing Sheets

(58) Field of Classification Search
CPC . G06T 2207/20084; G06T 2207/30268; G06T 7/0016; A61B 5/02416; A61B 5/6893; A61B 2503/22; A61B 5/0077; A61B 5/7267; A61B 5/024
See application file for complete search history.

(56) References Cited

U.S. PATENT DOCUMENTS

| | | | | |
|---|---|---|---|---|
| 2018/0303434 | A1* | 10/2018 | Selvaraj | A61B 5/318 |
| 2019/0046057 | A1* | 2/2019 | Lai | G06K 9/00234 |
| 2020/0163560 | A1* | 5/2020 | Chang | A61B 5/1102 |

FOREIGN PATENT DOCUMENTS

| | | |
|---|---|---|
| TW | I527560 B | 4/2016 |
| TW | I568411 B | 2/2017 |
| TW | I588674 B | 6/2017 |
| TW | M543052 U | 6/2017 |
| TW | M543672 U | 6/2017 |

OTHER PUBLICATIONS

De Haan et al., "Robust pulse-rate from chrominance-based rPPG," IEEE Transactions on Biomedical Engineering, 2013, pp. 1-9.
Poh et al., "Advancements in Noncontact, Multiparameter Physiological Measurements Using a Webcam," IEEE Transactions on Biomedical Engineering, vol. 58, No. 1, Jan. 2011, pp. 7-11.

\* cited by examiner

PHYSIOLOGICAL INFORMATION DETECTION DEVICE AND PHYSIOLOGICAL INFORMATION DETECTION METHOD

BACKGROUND

Technical Field

The present invention relates to a physiological information detection device and a physiological information detection method, and in particular, to a physiological information detection device and a physiological information detection method for detecting a physiological value by using a dynamic image.

Related Art

Driving safety is the goal that people have always been devoted to achieve. In recent years, with the development of vehicle electronic products, more diversified auxiliary functions have been provided for the drivers to ensure driving safety. For example, a lane departure warning system, a vehicle backup camera and the like are all auxiliary functions that can help a driver to be effectively aware of the outside circumstance to improve driving safety.

However, in addition to factors of a vehicle itself and the circumstance outside the vehicle, the physiological status of a driver is also an important factor for driving safety. For example, it is well-known that fatigue driving has always been one of the main causes of traffic accidents. Many drivers have to drive for a long time due to work requirements. Over time, this increases not only the risk of diseases, but also the possibility to make mistakes during driving. In addition, traffic accidents caused by attacks of diseases, elderly drivers and other factors are also always a focus of attention. Therefore, how to detect physiological information such as a heart rate of a driver in real time has become one of the main subjects into which researchers put tremendous efforts currently.

SUMMARY

The Technical Means to Solve the Problem

To solve the above problem, the present invention provides a physiological information detection device and a physiological information detection method that can, for example, detect physiological information such as a physiological value of a subject, and also can reduce noise caused by environmental factors.

According to an embodiment of the present invention, a physiological information detection method is provided to detect physiological information of a subject. The detection method includes: detecting a dynamic image of the subject and acquiring detection data from the dynamic image, where the detection data include a plurality of time-ordered data blocks and each data block is a gray-scale value of the dynamic image in a different time period; acquiring a plurality of frequency data from the detection data through transformation, where each frequency data includes a frequency distribution and a frequency intensity of a data block; and when a frequency data meets a preset condition, the frequency data is transformed by using a corresponding transformation combination, where the transformation combination includes a plurality of transformation models and the transformation models correspond to different transformation intervals. The transformation intervals are differentiated based on physiological values detected at previous moments. In the detection method, the frequency data meeting the preset conditions is transformed using a transformation model corresponding to a transformation interval to which a physiological value detected at a previous moment belongs, so as to acquire a physiological value corresponding to the frequency data.

According to an embodiment of the present invention, the corresponding transformation combination is selected according to a testing time to transform the frequency data. The testing time is a cumulative time after the preset condition is met. A plurality of time intervals corresponds to different transformation combinations. Selecting the corresponding transformation combination includes selecting the corresponding transformation combination according to a time interval to which the testing time belongs.

According to another embodiment of the present invention, when a testing time, which is a cumulative time after the preset condition is met, falls within a specific range, a transformation model used at a previous moment is modified and then used to transform the frequency data to acquire the physiological value.

According to another embodiment of the present invention, the step of acquiring the detection data includes: determining a detection region in each image frame of the dynamic image. The detection data include a plurality of time-ordered detection values, and each detection value is a linear combination of gray-scale values in the detection region of the image frame.

According to another embodiment of the present invention, the detection region corresponds to a preset region on the subject's face.

According to another embodiment of the present invention, the step of acquiring the detection data further includes: adding up gray-scale values of the detection region of each image frame of the dynamic image and dividing the sum by the area of the detection region, so as to acquire a detection value.

According to another embodiment of the present invention, the physiological value is a heart rate value of the subject.

According to another embodiment of the present invention, the frequency distribution and the frequency intensity of the data block are acquired from the data block through fast Fourier transform.

According to another embodiment of the present invention, the preset condition is that: a spectral entropy of the frequency data exceeds an entropy threshold and the spectral entropy meets the following equation:

$$PSE = \sum_{i=1}^{n} |f_i| \times \log_2(|f_i|)$$

where PSE is the spectral entropy and $f_i$ is a frequency value in the frequency data.

According to another embodiment of the present invention, the preset condition is that a spectral entropy of the frequency data exceeds an entropy threshold and when the spectral entropy of the frequency data is less than the entropy threshold, the physiological value is acquired by setting a frequency with the largest intensity in the frequency data as the physiological value.

According to another embodiment of the present invention, when a testing time, which is a cumulative time after the preset condition is met, is less than a first preset time, frequencies with top n intensities in the frequency data are input into a first transformation combination, and a transformation model of a corresponding transformation interval in the first transformation combination is selected according to the physiological value detected at the previous moment, so as to acquire the physiological value through transformation. n may be 30.

According to another embodiment of the present invention, when a testing time, which is a cumulative time after the preset condition is met, is greater than the first preset time and less than a second preset time, the frequencies with top n intensities in the frequency data are input into a second transformation combination, and a transformation model of a corresponding transformation interval in the second transformation combination is selected according to a physiological value detected at the previous moment, so as to acquire the physiological value through transformation. n may be 30.

According to another embodiment of the present invention, when a testing time, which is a cumulative time after the preset condition is met, is greater than the second preset time, an initial physiological value at the beginning of the detection method is selected and output as the physiological value.

According to an embodiment of the present invention, the transformation models are acquired in advance through artificial neural network training based on at least one known physiological value and at least one known frequency data.

According to an embodiment of the present invention, a physiological information detection device applying the foregoing detection method to detect physiological information of a subject is provided.

According to an embodiment of the present invention, a physiological information detection device is provided to detect physiological information of a subject. The detection device includes: an image capturing module for detecting a dynamic image of the subject; a frequency signal transformation module for acquiring detection data from the dynamic image and acquiring a plurality of frequency data from the detection data through transformation, where the detection data include a plurality of time-ordered data blocks, each data block is a gray-scale value of the dynamic image in a different time period, and each frequency data includes a frequency distribution and a frequency intensity of a data block; and a physiological signal transformation module, storing or capable of accessing at least one transformation combination and an initial physiological value. The physiological signal transformation module determines whether the frequency data meet a preset condition, and when a frequency data meets the preset condition, transforms the frequency data by using a corresponding transformation combination. The transformation combination includes a plurality of transformation models. The transformation models correspond to different transformation intervals. The transformation intervals are differentiated based on different initial physiological values or physiological values detected at previous moments. The physiological signal transformation module uses a transformation model corresponding to a transformation interval to which an initial physiological value or a physiological value detected at a previous moment belongs, to transform the frequency data meeting the preset condition, so as to acquire a physiological value corresponding to the frequency data.

According to an embodiment of the present invention, the physiological signal transformation module selects a corresponding transformation combination according to a testing time to transform the frequency data. The testing time is a cumulative time after the preset condition is met and a plurality of time intervals corresponds to different transformation combinations. The physiological signal transformation module may select the corresponding transformation combination according to a time interval to which the testing time belongs.

According to another embodiment of the present invention, when a testing time, which is a cumulative time after the preset condition is met, falls within a specific range, the physiological signal transformation module may modify a transformation model used at a previous moment and then use the modified transformation model to transform the frequency data to acquire the physiological value.

According to another embodiment of the present invention, the image capturing module determines a detection region in each image frame of the dynamic image, and the detection data acquired by the frequency signal transformation module include a plurality of time-ordered detection values. Each detection value is a linear combination of gray-scale values in the detection region of the image frame.

According to another embodiment of the present invention, the detection region corresponds to a preset region on the subject's face.

According to another embodiment of the present invention, the frequency signal transformation module may add up gray-scale values of the detection region of each image frame of the dynamic image and divide the sum by the area of the detection region, so as to acquire a detection value.

According to another embodiment of the present invention, the physiological value is a heart rate value of the subject.

According to another embodiment of the present invention, the frequency distribution and the frequency intensity of the data block are acquired from the data block by the frequency signal transformation module through fast Fourier transform.

According to another embodiment of the present invention, the preset condition is that: a spectral entropy of the frequency data exceeds an entropy threshold, and the spectral entropy meets the following equation:

$$PSE = \sum_{i=1}^{n} |f_i| \times \log_2(|f_i|)$$

where PSE is the spectral entropy and $f_i$ is a frequency value in the frequency data.

According to another embodiment of the present invention, the preset condition is that: a spectral entropy of the frequency data exceeds an entropy threshold. When the spectral entropy of the frequency data is less than the entropy threshold, the physiological signal transformation module may acquire the physiological value by setting a frequency with the largest intensity in the frequency data as the physiological value.

According to another embodiment of the present invention, when a testing time, which is a cumulative time after the preset condition is met, is less than a first preset time, the physiological signal transformation module inputs frequencies with top 30 intensities in the frequency data into a first transformation combination, and selects a transformation model of a corresponding transformation interval in the first transformation combination according to the physiological value detected at the previous moment, so as to acquire the physiological value through transformation.

According to another embodiment of the present invention, when a testing time, which is a cumulative time after the preset condition is met, is greater than the first preset time and less than a second preset time, the physiological signal transformation module inputs the frequencies with top 30 intensities in the frequency data into a second transformation combination, and selects a transformation model of a corresponding transformation interval in the second transformation combination according to the physiological value detected at the previous moment, so as to acquire the physiological value through transformation.

According to another embodiment of the present invention, when a testing time, which is a cumulative time after the preset condition is met, is greater than the second preset time, the physiological signal transformation module selects and outputs an initial physiological value as the physiological value.

According to another embodiment of the present invention, the transformation models are acquired in advance through artificial neural network training based on at least one known physiological value and at least one known frequency data.

Effects Compared to the Prior Art

It can be known from the above that the physiological information detection method and/or the physiological information detection device provided in the embodiments of the present invention can acquire a physiological value of a subject from gray-scale changes of a dynamic image by using different transformation models of different transformation combinations, thereby reducing the affects of environmental noise. Therefore, the physiological information detection method and/or the physiological information detection device provided in the embodiments of the present invention can be used to improve the accuracy and stability of the physiological value detected from the dynamic image.

DETAILED DESCRIPTION

The following describes various embodiments, and for a person of ordinary skill in the art, the spirit and principle of the present invention are readily to understand with reference to the descriptions in conjunction with the accompanying drawings. However, although some specific embodiments are described in detail herein, these embodiments are merely exemplary and are neither limitive nor exhaustive in any aspect. Therefore, for a person of ordinary skill in the art, it is apparent and easy to make various alterations and modifications to the present invention without departing from the spirit and principle of the present invention.

A device implementing the physiological information detection method or the physiological information detection device provided in the present invention may be a portable electronic device such as a smartphone, a tablet computer or a notebook computer, or may be an electronic device such as a high-efficiency car computer, or a high-efficiency computer mounted on a plane or other transportation vehicles. For the purpose of convenient and brief description, a car computer is used as an example for description below. A person of ordinary skill in the art should understand that the physiological information detection method and the physiological information detection device according to the embodiments of the present invention are not limited thereto.

Figure 1A:
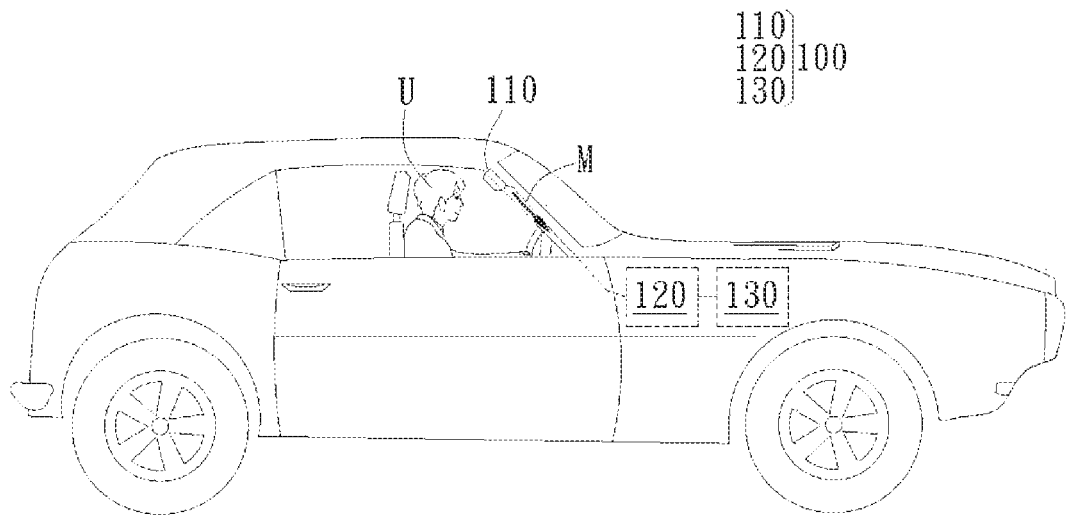
FIG. 1A is a schematic diagram of a physiological information detection device according to an embodiment of the present invention.

As described above, FIG. 1A is a schematic diagram of a physiological information detection device 100 used to detect physiological information of a subject according to an embodiment of the present invention. Referring to FIG. 1A, the physiological information detection device 100 includes an image capturing module 110, a frequency signal transformation module 120 and a physiological signal transformation module 130. For example, the frequency signal transformation module 120 and the physiological signal transformation module 130 may be, or include, a central processing unit (CPU) of a car computer or other electronic devices capable of performing calculation processing. The image capturing module 110 may be or include a camera device connected to a car computer, for example, may be a light-sensitive component such as a charge-coupled device (CCD) or a complementary metal-oxide semiconductor (CMOS), and the present invention is not limited thereto. In addition, in some embodiments, the image capturing module 110, the frequency signal transformation module 120 and the physiological signal transformation module 130 may use one or more same calculators or processing units, and the present invention is not limited thereto.

Based on the physiological information detection device 100, the following further describes the physiological information detection method according to an embodiment of the present invention.

Figure 1B:
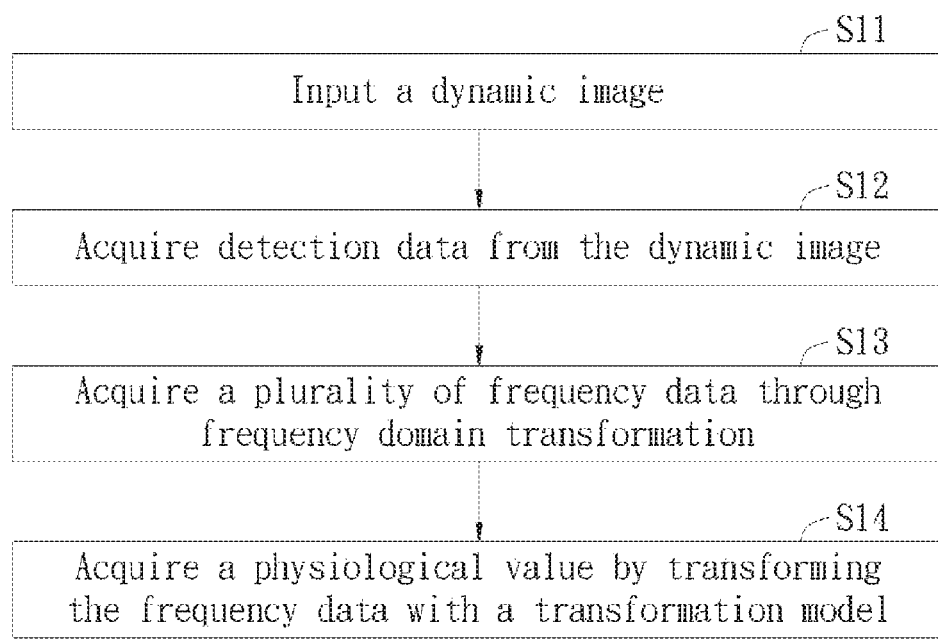
FIG. 1B is a schematic flowchart of a physiological information detection method according to an embodiment of the present invention.

As described above, generally, further referring to FIG. 1A and FIG. 1B together, according to an embodiment of the present invention, the image capturing module 110 may be configured to detect (for example, capture) a dynamic image M of a subject U, and the dynamic image M is transmitted from the image capturing module 110 and input into the frequency signal transformation module 120 (step S11). Then, the frequency signal transformation module 120 may acquire detection data from the dynamic image (step S12) and acquire a plurality of frequency data from the detection data through, for example, frequency domain transformation (step S13). Finally, the physiological signal transformation module 130 acquires a needed physiological value by transforming the frequency data by using a corresponding transformation model or a transformation mode (step S14).

In short, according to an embodiment, frequency domain analysis may be performed on the detection data to acquire the frequency data after the detection data is acquired from a gray-scale value of the dynamic image M, and whether the frequency data meet a preset condition is determined to acquire the physiological value by using a corresponding transformation model. The preset condition is, for example, whether the frequency data reach a preset degree of randomness, and random signals may be adjusted to acquire proper physiological information in the present invention. The gray-scale value is, for example, a sum of three primary colors values (RGB values) in the image weighted in different weight values. For example, the gray-scale value may be R*0.299+G*0.587+B*0.114. R is a value of the red color, G is a value of the green color and B is a value of the blue color, but the present invention is not limited thereto. In other embodiments, the used three primary colors values (RGB values) or gray-scale intensity values may be adjusted according to a demand or a characteristic of the image (for example, when the image is black and white).

According to an embodiment of the present invention, based on the above steps, the following further describes the physiological information detection device and the physiological information detection method in detail sequentially. However, the case that the physiological value is a heart rate value of the subject is used only as an example, and the present invention is not limited thereto.

Figure 2A:
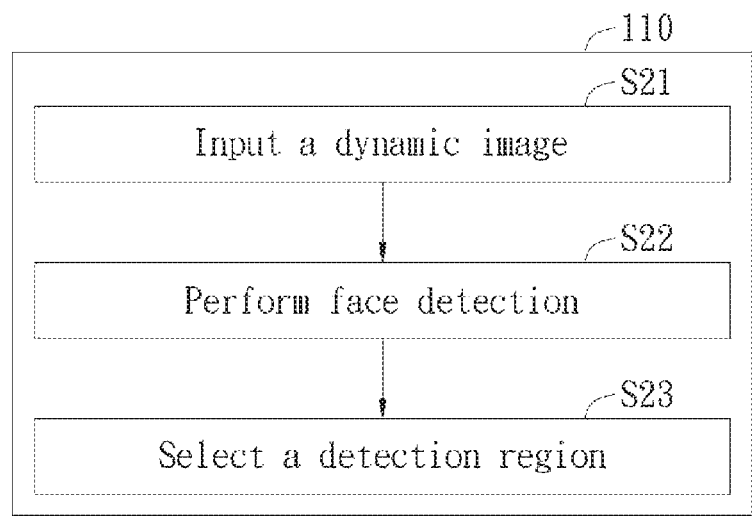
FIG. 2A is a schematic flowchart of performing detection according to an embodiment of the present invention.
Figure 2B:
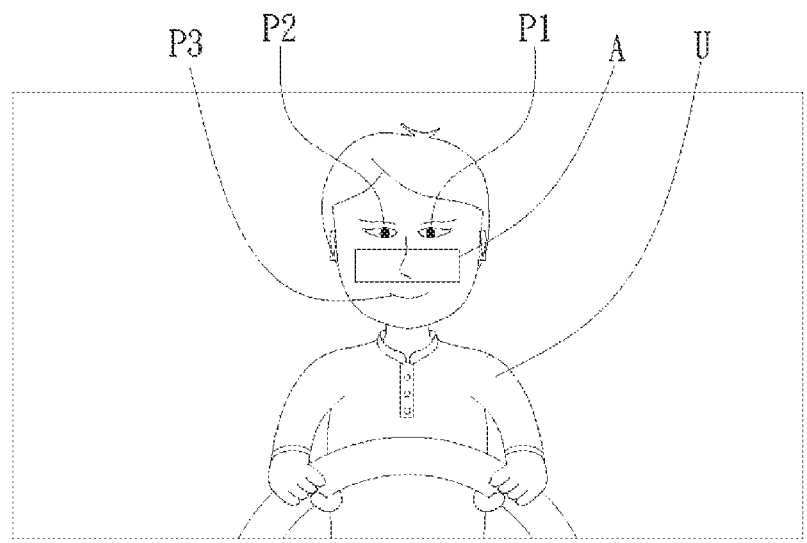
FIG. 2B is a schematic diagram of selecting a detection region according to an embodiment of the present invention.

Referring to the flowchart in FIG. 2A, the same or similar symbols in FIG. 1A will be still used for the following devices for ease of description. As described above, before acquiring the detection data, the image capturing module 110 may be used to capture and input the dynamic image M including a plurality of successive images (step S21). In addition, according to some embodiments of the present invention, the image capturing module 110 may further perform face detection on these images (step S22). Specifically, referring to FIG. 2A and FIG. 2B together, the image capturing module 110 may perform face detection on the successive static images respectively in the dynamic image M, so as to find out images corresponding to the face of the subject U from the static images (step S22). For example, the image capturing module 110 finds out positions P1, P2 and P3 respectively corresponding to the eyes and the mouth of the subject through facial contour detection, so as to detect the face. Then, the image capturing module 110 may select a detection region A of interest (step S23). For example, the detection region A of interest may be a preset region on the face such as an area between the eyes and the mouth, so as to avoid unnecessary image changes caused by speaking or blinking of the subject. In addition, according to other embodiments of the present invention, steps S22 and S23 may also be performed by the frequency signal transformation module 120, and the present invention is not limited thereto.

As described above, by determining the detection region A of interest, when the dynamic image M is input into the frequency signal transformation module 120, the range that requires image processing or calculation subsequently can be reduced. Therefore, efforts for the frequency signal transformation module 120 to perform image processing or calculation on all the images of the entire screen can be reduced or omitted, thereby reducing overall calculation time or power consumption.

In some embodiments, the accuracy of the facial contour detection may be improved by using the architecture such as the Multi-task Cascaded Convolutional Network and a face database WIDER FACE. The face database WIDER FACE includes a plurality of pictures taken in actual occasions, from different angles and with different sizes, poses, face decorations, light and shadow changes, and the like. Therefore, in addition to reducing overall calculation by selecting the detection region A, image training with respect to the above factors can also improve the accuracy of the face detection and reduce misjudgments caused by light and shadow changes.

The foregoing method related to the face detection and the detection region is merely exemplary and not intended to limit the present invention. In other embodiments, other face detection or facial contour detection methods may also be used to process these images. The size and shape of the detection region A certainly can be selected and adjusted according to a demand or efficiency of a system, and the present invention is not limited thereto.

Figure 3:
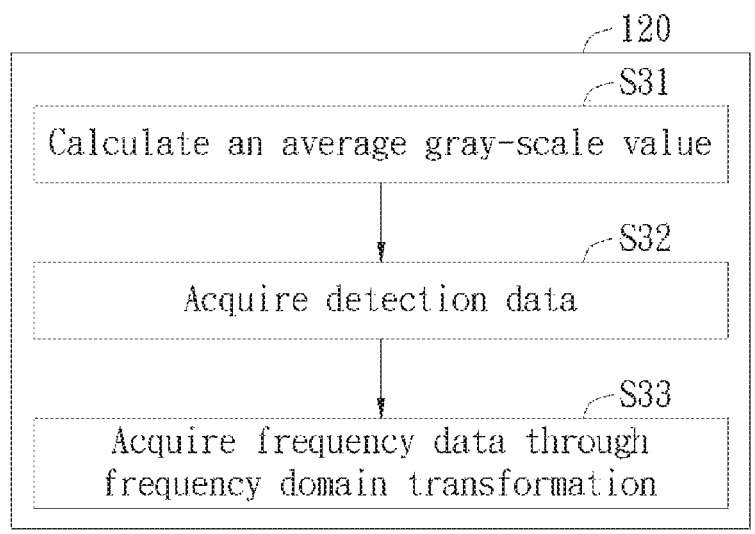
FIG. 3 is a schematic flowchart of transforming detection data into frequency data according to an embodiment of the present invention.

Then, according to an embodiment of the present invention, in the physiological information detection method and/or the physiological information detection device 100, calculation of a time domain physiological value is performed based on changes of the gray-scale value in the detection region A. Therefore, unneeded signals and noise can be reduced through calculation of the time domain physiological value, so as to acquire better and undistorted detection data. For example, referring to FIG. 3, after the dynamic image M is input into the frequency signal transformation module 120, the frequency signal transformation module 120 may calculate and record a plurality of detection values with time based on the detection region A, where the detection value may be an average gray-scale value (step S31), and then acquire the detection data (step S32).

For example, when the physiological value is a heart rate value, the static images of the subject U may be formed from reflected light and diffused light from the skin of the subject. When blood circulates in the body of the subject, the volume of capillaries changes with time and the diffused light that is absorbed by the skin and then diffused changes with the volume of capillaries, so that the diffused light can carry heartbeat information of the subject. By the contrast, the reflected light is a light beam directly reflected by the skin of the body and does not carry the related heartbeat information. The intensity of the reflected light may be greater than that of the diffused light. Therefore, according to an embodiment of the present invention, the detection value may be, for example, an average gray-scale value calculated by the frequency signal transformation module 120 adding up the gray-scale values in the detection region A of each image frame (that is, the static image described above) of the dynamic image M and dividing the sum by the area of the detection region A, thereby the change in the diffused light (reflecting the change in the heart rate value) can be emphasized through averaging.

As described above, in this embodiment, based on the detection values calculated and recorded in step S31, the detection data acquired in step S32 may include a plurality of time-ordered data blocks. Each data block is a gray-scale value of the dynamic image M in a different time period. In addition, in some embodiments, the detection data may include a plurality of time-ordered detection values, and each detection value is a linear combination of gray-scale values in the detection region A of the image frame.

Then, after calculation of time domain detection data is completed, the frequency signal transformation module 120 may further perform frequency domain transformation on the calculated detection data. In detail, the frequency signal transformation module 120 in this embodiment may acquire the frequency data by performing frequency domain transformation on the plurality of data blocks of the detection data according to the time order (step S33). For example, each data block includes 512 processed detection values.

Each frequency data is a frequency distribution and a frequency intensity of the data block. For example:

$$\vec{F_t} = [f_{k,t} | S_R(f_{k,t})|],$$

For example, each data block includes 512 processed detection values. Each frequency data is a frequency distribution and a frequency intensity of the data block. For example:

$$f_k = F\{S_t\}$$

where k may be 1 to m, m is a preset number of frequencies to be selected, t is 1 to T, T is a preset number of time-ordered data blocks, $S_t$ is a time domain detection data block, and $f_k$ is frequency data after frequency domain transformation is performed.

In some embodiments, time domain detection signals (detection data) may be transformed into frequency data through fast Fourier transform (FFT) for analysis. For example, a frequency distribution and a frequency intensity of a data block are acquired from the data block through fast Fourier transform, but the present invention is not limited thereto. In other embodiments, for a person of ordinary skill in the art, transformation between time domain detection signals (detection data) and frequency data may be implemented in different manners according to different demands, which is not further described herein.

Figure 4:
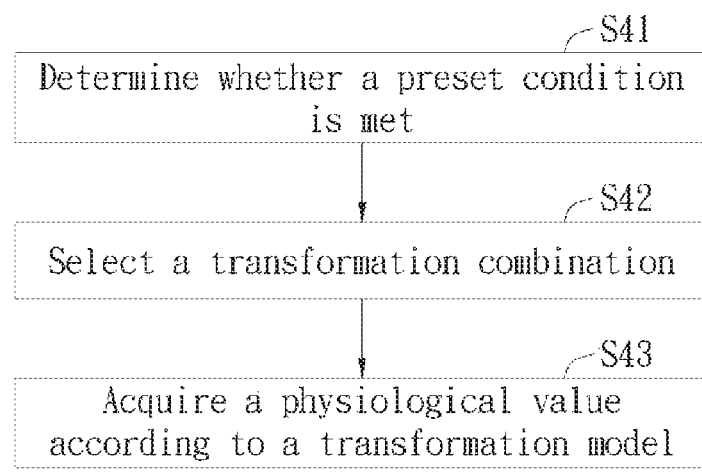
FIG. 4 is a general schematic flowchart of acquiring a physiological value from frequency data according to an embodiment of the present invention.

Then, referring to FIG. 4, in the physiological information detection method and the physiological information detection device in this embodiment, whether to perform the subsequent steps is determined according to whether the frequency data meet a preset condition. In detail, the physiological signal transformation module 130 may determine whether the frequency data meet the preset condition, so as to determine whether the degree of randomness of the frequency data reaches a threshold (that is, the preset condition). When the dynamic image M of the subject U is captured in an environment with bright light and no light and shadow changes, detection data and frequency data acquired from the dynamic image M more directly reflect the person's physiological information such as a heart rate value. However, if the degree of randomness of the frequency data reaches a threshold, it indicates that there is insufficient light or significant large light and shadow changes in the surrounding environment of the subject U, detection data and frequency data acquired from the dynamic image M are prone to distortion, and subsequent steps are needed for adjustment and calculation so as to acquire a physiological value such as a heart rate value more accurately.

For example, the preset condition may be whether the frequency data reach a preset degree of randomness, and preferably, whether a spectral entropy of the frequency data exceeds an entropy threshold, and the spectral entropy meets the following equation:

$$PSE = \sum_{i=1}^{n} |f_i| \times \log_2(|f_i|)$$

where PSE is the spectral entropy and $f_i$ is a frequency value in the spectral data.

As described above, the physiological information detection method and/or the physiological information detection device 100 according to this embodiment can determine whether the frequency data meet the preset condition according to whether the spectral entropy is greater than the entropy threshold (step S41), select a corresponding transformation combination or mode according to a determining result (step S42), and then transform the frequency data by using a corresponding transformation model in the transformation combination or a corresponding transformation mode to acquire the physiological value (step S43).

Figure 5:
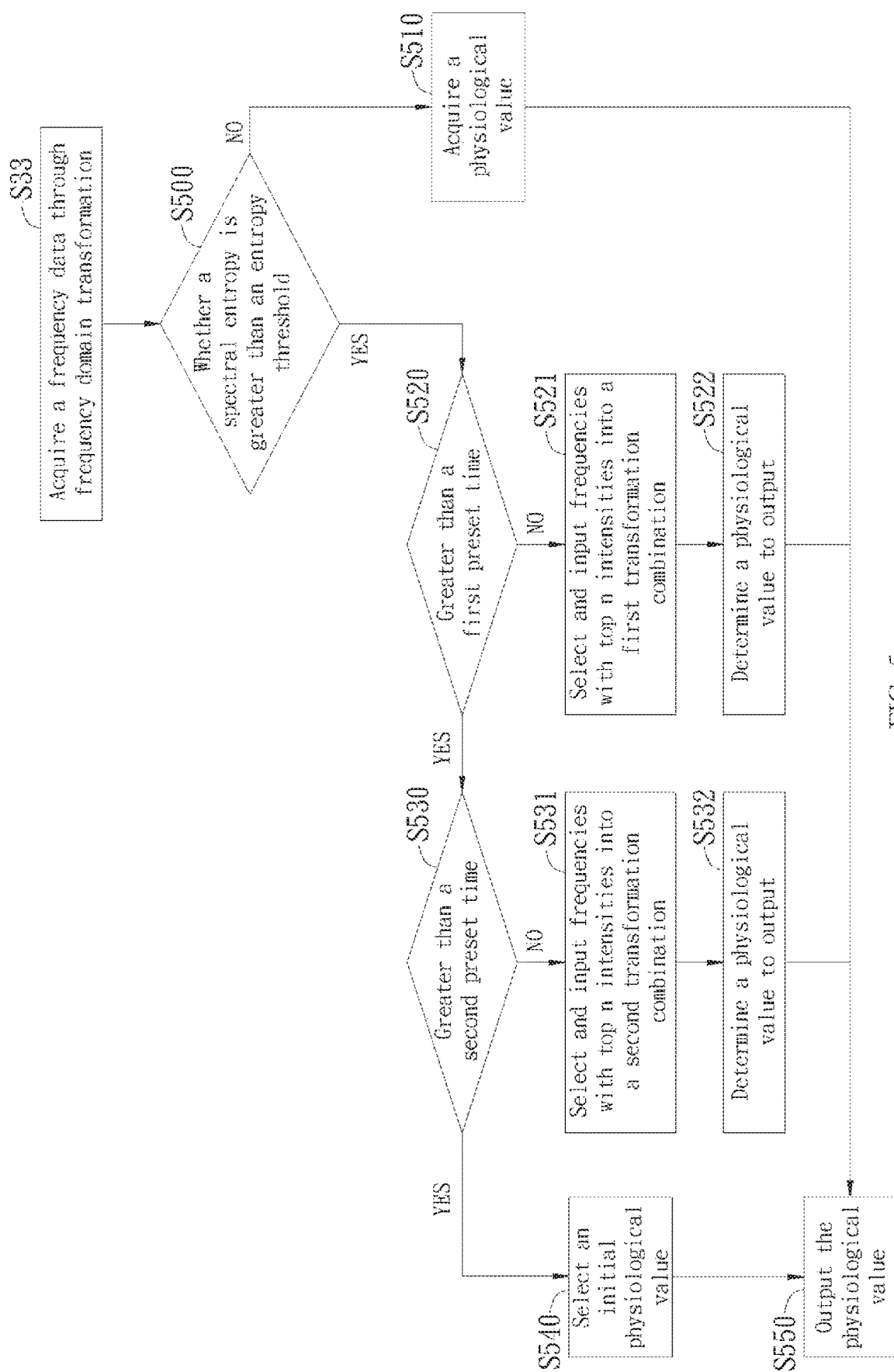
FIG. 5 is a detailed schematic flowchart of acquiring a physiological value from frequency data according to an embodiment of the present invention.

Specifically, referring to FIG. 5, after acquiring the frequency data through, for example, frequency domain transformation (step S33), it may be determined whether the spectral entropy is greater than the entropy threshold, that is, whether the frequency data meet the preset condition (step S500). After the frequency data meet the preset condition (for example, the spectral entropy is greater than the entropy threshold), a testing time which is a cumulative time after the preset condition is met begins to be calculated, and a corresponding transformation combination is selected according to the testing time to transform the frequency data. According to an embodiment, transforming the frequency data according to the corresponding transformation combination includes: transforming the frequency data according to a transformation model in the transformation combination to acquire the physiological value.

In detail, according to an embodiment of the present invention, a cumulative time after the preset condition is met can be divided into a plurality of time intervals and the plurality of time intervals corresponds to different transformation combinations. In the physiological information detection method and/or the physiological information detection device 100 according to the present invention, selecting the corresponding transformation combination may include: selecting the corresponding transformation combination according to a time interval to which the testing time belongs.

In addition, each transformation combination may include a plurality of transformation models, and the transformation models respectively correspond to different transformation intervals. In detail, the transformation intervals are differentiated based on different initial physiological values or physiological values detected at previous moments. That is, after a corresponding transformation combination is selected, the physiological signal transformation module 130 may use a transformation model corresponding to a transformation interval to which an initial physiological value or a physiological value detected at a previous moment belongs, to transform the frequency data meeting the preset condition, so as to acquire a physiological value corresponding to the frequency data.

For example, referring to the following Table 1, two transformation combinations include total 20 transformation models. A first transformation combination includes 16 transformation models, D1 to D16. A second transformation combination includes 4 transformation models, H1 to H4. After a transformation combination is selected, a corresponding transformation model may be selected to transform the frequency data according to a physiological value detected at a previous moment (if detection is not performed at a previous moment, an initial physiological value is used). For example, a transformation model D6 is a suitable transformation model for transforming the frequency data and calculating a corresponding current physiological value if a physiological value such as a heart rate interval detected at a previous moment falls within intensity values from 70 to 75. The following describes examples with more detailed flowcharts.

TABLE 1

| Transformation model | Heart rate interval | Transformation model | Heart rate interval |
|---|---|---|---|
| D1  | (0, 40)  | D11 | (95, 100)  |
| D2  | (40, 50) | D12 | (100, 105) |
| D3  | (50, 60) | D13 | (105, 110) |
| D4  | (60, 65) | D14 | (110, 120) |
| D5  | (65, 70) | D15 | (120, 130) |
| D6  | (70, 75) | D16 | (130, 200) |
| D7  | (75, 80) | H1  | (0, 50)    |
| D8  | (80, 85) | H2  | (50, 80)   |
| D9  | (85, 90) | H3  | (80, 110)  |
| D10 | (90, 95) | H4  | (110, 200) |

For example, referring to FIG. 5, when the spectral entropy of the frequency data does not exceed the entropy threshold, that is, the preset condition is not met (step S500), the physiological signal transformation module 130 may perform further multiple frequency filtering on the frequency data, use Kalman filter to smooth an output physiological value after setting the measurement time to zero, and further filter out noise. The physiological value obtained after the Kalman filter is used is the output physiological value (step S510), but the present invention is not limited thereto. For example, referring to FIG. 6, in step S510, the physiological value may be acquired by directly setting a frequency with the largest intensity in the frequency data as the physiological value.

Figure 6:
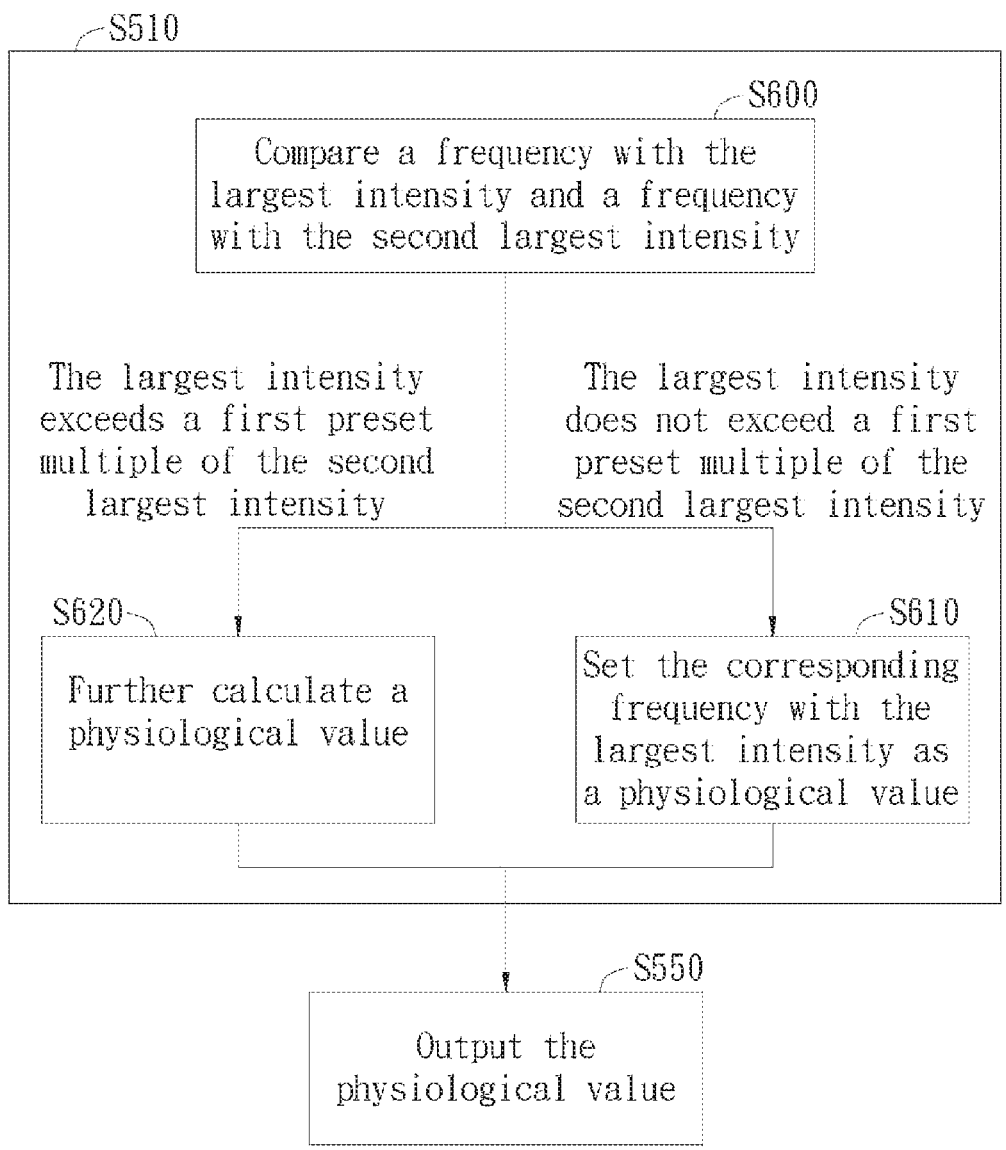
FIG. 6 is a schematic flowchart of acquiring a physiological value when a spectral entropy is less than an entropy threshold according to an embodiment of the present invention.

In detail, as shown in FIG. 6, in step S600, the physiological signal transformation module 130 may first compare a frequency with the largest intensity and a frequency with the second largest intensity. When the largest intensity does not exceed a first preset multiple (such as 1.5 times) of the second largest intensity (step S610), the frequency with the largest intensity may be directly set as the physiological value. When the largest intensity exceeds the first preset multiple (such as 1.5 times) of the second largest intensity (step S620), additional processing and calculation may be performed. For example, normalized values of the largest intensity and the second largest intensity may be compared. A normalized value is obtained by dividing a maximum value of frequency intensities by the sum of the frequency intensities of all the frequencies. When the absolute value of the normalized value of the second largest intensity does not exceed a second preset multiple of the absolute value of the normalized value of the largest intensity, the frequency with the largest intensity is set as the physiological value. When the absolute value of the normalized value of the second largest intensity exceeds the second preset multiple of the absolute value of the normalized value of the largest intensity, fundamental frequencies of the frequency with the largest intensity and the frequency with the second largest intensity are acquired. Then, when a difference between the frequency with the largest intensity and the fundamental frequency exceeds a difference between the frequency with the second largest intensity and the fundamental frequency, the initial physiological value is acquired by using the frequency with the second largest intensity; and when the difference between the frequency with the largest intensity and the fundamental frequency does not exceed the difference between the frequency with the second largest intensity and the fundamental frequency, the initial physiological value is acquired by using the frequency with the largest intensity. However, these are merely examples and the present invention is not limited thereto.

As described above, in some embodiments of the present invention, when there is a plurality of maximum values in the frequency intensities of the frequency data, the physiological signal transformation module 130 may compare two largest maximum values. If the largest maximum value does not exceed the preset first multiple of the second largest maximum value, a processing unit acquires the initial physiological value from the frequency corresponding to the largest maximum value.

Referring to FIG. 5 again, when the testing time, which is a cumulative time after the preset condition is met, is less than a first preset time (step S520), frequencies with top n intensities (for example, top 30 intensities) in the frequency data are input into a first transformation combination (step S521). The first transformation combination includes a plurality of transformation models (for example, transformation models D1 to D16). A transformation model of a corresponding transformation interval in the first transformation combination is selected according to a physiological value detected at a previous moment or an initial physiological value, so as to transform the frequency data to acquire the physiological value (step S522).

Further, when the testing time, which is a cumulative time after the preset condition is met, is greater than the first preset time and less than a second preset time (step S530), frequencies with top n intensities (for example, top 30 intensities) in the frequency data are input into a second transformation combination (step S531). The second transformation combination includes a plurality of transformation models (for example, transformation models H1 to H4). A transformation model of a corresponding transformation interval in the second transformation combination is selected according to a physiological value detected at a previous moment or an initial physiological value, so as to transform the frequency data to acquire the physiological value (step S532).

For example, if the transformation model is selected when a physiological value detected before the frequency data meet the preset condition or when a physiological value detected at a previous moment is 73, after the frequency data meet the preset condition, and a time unit does not exceed the first preset time, the physiological value is acquired by using a transformation model D6 to transform the frequency data, and when the time unit exceeds the first preset time and less than the second preset time, the physiological value is acquired by using a transformation model H2 to transform the frequency data.

In addition, when the testing time, which is a cumulative time after the preset condition is met, is greater than the second preset time (step S530), an initial physiological value at the beginning of the detection method is selected (step S540) and directly output as the physiological value.

Further, according to other embodiments of the present invention, when the testing time, which is a cumulative time after the preset condition is met, falls within a specific range, a transformation model used at a previous moment is modified and then directly used to transform the frequency data to acquire the physiological value.

As described above, the physiological information detection device and the physiological information detection method according to the embodiments of the present invention can select a suitable transformation model or a transformation mode to adjust and transform the processing and calculation mode of the frequency data in terms of time domain and output the physiological value accordingly (step S550), thereby acquiring the physiological value that is less interfered by noise.

The at least one transformation combination and the initial physiological value may be stored in the physiological signal transformation module 130, or at least may be accessed by the physiological signal transformation module 130.

In some embodiments, band-pass filtering may further be performed on the detection data. The range of the band-pass filtering is a physiological value range (such as a heart rate range) of a healthy normal person. An autocorrelation function may be used to modify the detection data.

In other aspects, the transformation models described above may be acquired in advance by the physiological signal transformation module 130 through artificial neural network training based on at least one known physiological value and at least one known frequency data.

For example, when the plurality of frequency data is acquired according to the dynamic image, a plurality of time-ordered physiological values is also acquired. Each frequency data and a corresponding physiological value thereof are split in pairs and transformed to be represented by a same frequency unit (such as Hz herein). Then the frequency data and the physiological values are classified into training data, generalization data and validation data, such as by accounting for 60%, 20% and 20% respectively. In addition to an input layer and an output layer, seven hidden layers may be used as the network architecture in this embodiment. The numbers of neurons on each layer are respectively 30, 20, 10, 10, 10, 20 and 30. All neurons on each layer are connected to all neurons on a neighboring layer.

In addition, for example, a learning rate in the artificial neural network training is set to 0.05. Momentum is set to 0.8. Weight decay is set to 0.001. A maximum quantity of iterations is 1000. An activation function of the input layer and the hidden layers is a piecewise linear ReLU function. An activation function of the output layer is a Purnlin function. The training data are input into the model in a growth manner. The growing size is 5%. The training data accounting for 5% are gradually expanded to training data accounting for 100%. After all the training data are trained, the validation data are used to check the network learning effect. The target accuracy is set to 100%. The mean absolute error (MAE) of a predicted physiological value and a corresponding actual physiological value is calculated. If the MAE is less than 0.15 Hz, the training is determined to be successful. Otherwise the training and weight adjustment are continued. After the training is completed, the plurality of transformation models of the subject is stored in the physiological signal transformation module 130.

In short, in some embodiments of the present invention, the transformation models that the physiological signal transformation module 130 can store or access are acquired in advance in a training stage. In the training stage, the physiological signal transformation module 130 is connected to the frequency signal transformation module 120. The frequency signal transformation module 120 detects frequency values of the subject U. The physiological signal transformation module 130 acquires the transformation models by using the frequency values from the frequency signal transformation module 120 and corresponding actual physiological values through the artificial neural network training.

It can be know from the above that a transformation relationship between a known physiological value such as a heart rate and known frequency data may be speculated through an artificial neural network. The physiological information detection device and the physiological information detection method according to the embodiments of the present invention can select a suitable transformation combination according to the duration of randomness of the frequency data, so as to maintain a better detection effect of the dynamic image in different conditions.

It should be noted that whether the physiological signal transformation module 130 independently acquires the transformation models or acquires the transformation models through calculation by using other processing units is not limited in the present invention. In other words, when the physiological signal transformation module 130 is a high-efficiency car computer, the physiological signal transformation module 130 may periodically acquire the transformation models from the subject through artificial neural network training. However, when the physiological signal transformation module 130 is a central processing unit of a smartphone, these transformation models may be stored in or accessed by the physiological signal transformation module 130 after being calculated by a central processing unit of another electronic device, and the present invention is not limited thereto.

In summary, the physiological information detection device and the physiological information detection method according to the embodiments of the present invention can analyze the frequency of changes in gray-scale values in a dynamic image, determine the degree of randomness of the dynamic image according to frequency data, and use transformation models in different transformation combinations to transform the frequency data when the degree of randomness reaches a threshold (the transformation models are selected according to an initial physiological value or a physiological value at a previous moment). Therefore, the accuracy of the detected physiological value can be improved and the unintended influence on the physiological value by different environments and conditions can be reduced or avoided.

The above are merely some preferred embodiments of the present invention. It should be noted that various alterations and modifications may be made to the present invention without departing from the spirit and principle of the present invention. A person of ordinary skill in the art should understand that the present invention is defined by the appended claims, and all possible changes such as replacements, combinations, modifications and alterations complied with the intention of the present invention should all fall within the scope of the appended claims of the present invention.

SYMBOL DESCRIPTION

100: Detection device
110: Image capturing module
120: Frequency signal transformation module
130: Physiological signal transformation module
M: Dynamic image
U: Subject
P1, P2, P3: Positions
A: Detection region
S11-S14: Steps
S21-S23: Steps
S31-S33: Steps
S41-S43: Steps
S500, S510, S520, S521, S522, S530, S531, S532, S540, S550: Steps
S600, S610, S620: Steps

What is claimed is:
1. A physiological information detection method for detecting physiological information of a subject, wherein the detection method comprises:

detecting a dynamic image of the subject and acquiring detection data from the dynamic image, wherein the detection data comprise a plurality of time-ordered data blocks and each data block is a gray-scale value of the dynamic image in a different time period;

acquiring a plurality of frequency data from the detection data through transformation, wherein each frequency data comprises a frequency distribution and a frequency intensity of a data block; and when a frequency data of the plurality of frequency data meets a preset condition, transforming the frequency data by using a corresponding transformation combination, wherein the transformation combination comprises a plurality of transformation models, the transformation models respectively correspond to different transformation intervals, the transformation intervals are differentiated based on different physiological values detected at previous moments, and wherein the detection method uses the transformation model corresponding to the transformation interval to which the physiological value detected at a previous moment belongs, to transform the frequency data meeting the preset condition, so as to acquire a physiological value corresponding to the frequency data.

2. The detection method according to claim 1, wherein the corresponding transformation combination is selected according to a testing time to transform the frequency data, wherein the testing time is a cumulative time after the preset condition is met, and a plurality of time intervals corresponds to different transformation combinations, wherein selecting the corresponding transformation combination comprises selecting the corresponding transformation combination according to a time interval to which the testing time belongs.

3. The detection method according to claim 1, wherein when a testing time, which is a cumulative time after the preset condition is met, falls within a specific range, a transformation model used at a previous moment is modified and then used to transform the frequency data to acquire the physiological value.

4. The detection method according to claim 1, wherein the step of acquiring the detection data comprises:

determining a detection region in each image frame of the dynamic image, wherein the detection data comprise a plurality of time-ordered detection values, and each detection value is a linear combination of gray-scale values in the detection region of one of the image frame.

5. The detection method according to claim 4, wherein the detection region corresponds to a preset region on the subject's face.

6. The detection method according to claim 4, wherein the step of acquiring the detection data further comprises:

adding up gray-scale values of the detection region of each image frame of the dynamic image and dividing the sum by the area of the detection region, so as to acquire a detection value.

7. The detection method according to claim 1, wherein the physiological value is a heart rate value of the subject.

8. The detection method according to claim 1, wherein the frequency distribution and the frequency intensity of the data block are acquired from the data block through fast Fourier transform.

9. The detection method according to claim 1, wherein the preset condition is:

a spectral entropy of the frequency data exceeds an entropy threshold and the spectral entropy meets the following equation:

$$PSE = \sum_{i=1}^{n} |f_i| \times \log_2(|f_i|)$$

wherein PSE is the spectral entropy and $f_i$ is a frequency value in the frequency data.

10. The detection method according to claim 1, wherein the preset condition is that a spectral entropy of the frequency data exceeds an entropy threshold and when the spectral entropy of the frequency data is less than the entropy threshold, the physiological value is acquired by setting a frequency with the largest intensity in the frequency data as the physiological value.

11. The detection method according to claim 1, wherein when a testing time, which is a cumulative time after the preset condition is met, is less than a first preset time, frequencies with top 30 intensities in the frequency data are input into a first transformation combination, and a transformation model of a corresponding transformation interval in the first transformation combination is selected according to the physiological value detected at the previous moment, so as to acquire the physiological value through transformation.

12. The detection method according to claim 11, wherein when a testing time, which is a cumulative time after the preset condition is met, is greater than the first preset time and less than a second preset time, the frequencies with top 30 intensities in the frequency data are input into a second transformation combination, and a transformation model of a corresponding transformation interval in the second transformation combination is selected according to the physiological value detected at the previous moment, so as to acquire the physiological value through transformation.

13. The detection method according to claim 12, wherein when the testing time, which is the cumulative time after the preset condition is met, is greater than the second preset time, an initial physiological value at the beginning of the detection method is selected and output as the physiological value.

14. The detection method according to claim 1, wherein the transformation models are acquired in advance through artificial neural network training based on at least one known physiological value and at least one known frequency data.

15. A physiological information detection device for detecting physiological information of a subject, wherein the detection device comprises:

an image capturing module, detecting a dynamic image of the subject;

a frequency signal transformation module, acquiring detection data from the dynamic image and acquiring a plurality of frequency data from the detection data through transformation, wherein the detection data comprise a plurality of time-ordered data blocks, each data block is a gray-scale value of the dynamic image in a different time period, and each frequency data comprises a frequency distribution and a frequency intensity of a data block; and a physiological signal transformation module, storing or capable of accessing at least one transformation combination and an initial physiological value, wherein the physiological signal transformation module determines whether the frequency data meet a preset condition and when a frequency data meets the preset condition, transforms the frequency data by using a corresponding transformation combination, wherein the transformation combination comprises a plurality of transformation models, the transformation models respectively correspond to different transformation intervals, the transformation intervals are differentiated based on different initial physiological values or physiological values detected at previous moments, and the physiological signal transformation module uses the transformation model corresponding to the transformation interval to which the initial physiological value or the physiological value detected at a previous moment belongs, to transform the frequency data meeting the preset condition, so as to acquire a physiological value corresponding to the frequency data.

16. The physiological information detection device according to claim 15, wherein the physiological signal transformation module selects a corresponding transformation combination according to a testing time to transform the frequency data, wherein
the testing time is a cumulative time after the preset condition is met and a plurality of time intervals corresponds to different transformation combinations, wherein
the physiological signal transformation module selects the corresponding transformation combination according to a time interval to which the testing time belongs.

17. The physiological information detection device according to claim 15, wherein when a testing time, which is a cumulative time after the preset condition is met, falls within a specific range, the physiological signal transformation module modifies a transformation model used at a previous moment and then uses the modified transformation model to transform the frequency data to acquire the physiological value.

18. The physiological information detection device according to claim 15, wherein:
the image capturing module determines a detection region in each image frame of the dynamic image; and
the detection data acquired by the frequency signal transformation module comprise a plurality of time-ordered detection values, and each detection value is a linear combination of gray-scale values in the detection region of the image frame.

19. The physiological information detection device according to claim 18, wherein the detection region corresponds to a preset region on the subject's face.

20. The physiological information detection device according to claim 18, wherein the frequency signal transformation module adds up gray-scale values of the detection region of each image frame of the dynamic image and divides the sum by the area of the detection region, so as to acquire a detection value.

21. The physiological information detection device according to claim 15, wherein the physiological value is a heart rate value of the subject.

22. The physiological information detection device according to claim 15, wherein the frequency distribution and the frequency intensity of the data block are acquired from the data block by the frequency signal transformation module through fast Fourier transform.

23. The physiological information detection device according to claim 15, wherein the preset condition is:
a spectral entropy of the frequency data exceeds an entropy threshold, and the spectral entropy meets the following equation:

$$PSE = \sum_{i=1}^{n} |f_i| \times \log_2(|f_i|)$$

wherein PSE is the spectral entropy and $f_i$ is a frequency value in the frequency data.

24. The physiological information detection device according to claim 15, wherein the preset condition is that a spectral entropy of the frequency data exceeds an entropy threshold, and when the spectral entropy of the frequency data is less than the entropy threshold, the physiological signal transformation module acquires the physiological value by setting a frequency with the largest intensity in the frequency data as the physiological value.

25. The physiological information detection device according to claim 15, wherein when a testing time, which is a cumulative time after the preset condition is met, is less than a first preset time, the physiological signal transformation module inputs frequencies with top 30 intensities in the frequency data into a first transformation combination, and selects a transformation model of a corresponding transformation interval in the first transformation combination according to the physiological value detected at the previous moment, so as to acquire the physiological value through transformation.

26. The physiological information detection device according to claim 25, wherein when a testing time, which is a cumulative time after the preset condition is met, is greater than the first preset time and less than a second preset time, the physiological signal transformation module inputs the frequencies with top 30 intensities in the frequency data into a second transformation combination, and selects a transformation model of a corresponding transformation interval in the second transformation combination according to the physiological value detected at the previous moment, so as to acquire the physiological value through transformation.

27. The physiological information detection device according to claim 26, wherein when a testing time, which is a cumulative time after the preset condition is met, is greater than the second preset time, the physiological signal transformation module selects and outputs the initial physiological value as the physiological value.

28. The physiological information detection device according to claim 15, wherein the transformation models are acquired in advance through artificial neural network training based on at least one known physiological value and at least one known frequency data.

* * * * *